United States Patent
Rich

(10) Patent No.: US 7,981,661 B2
(45) Date of Patent: Jul. 19, 2011

(54) FLOW CYTOMETER SYSTEM WITH SHEATH AND WASTE FLUID MEASUREMENT

(75) Inventor: Collin A. Rich, Ypsilanti, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 1116 days.

(21) Appl. No.: 11/736,412

(22) Filed: Apr. 17, 2007

(65) Prior Publication Data

US 2007/0243106 A1 Oct. 18, 2007

Related U.S. Application Data

(60) Provisional application No. 60/792,447, filed on Apr. 17, 2006.

(51) Int. Cl.
*C12M 1/36* (2006.01)
*G01N 33/48* (2006.01)
*G01N 27/22* (2006.01)

(52) U.S. Cl. ............... 435/286.5; 435/286.1; 435/287.1; 435/287.3; 422/67; 422/68.1; 422/73; 422/82.01; 436/50; 436/63; 436/149; 436/150

(58) Field of Classification Search ............... 436/43, 436/50, 63, 149, 150, 164, 180; 422/67, 422/68.1, 73, 82.01, 82.05; 435/286.1, 286.5, 435/287.1, 287.3
See application file for complete search history.

(56) References Cited

U.S. PATENT DOCUMENTS

| | | | |
|---|---|---|---|
| 3,347,273 A | 10/1967 | Russell | |
| 3,601,128 A | 8/1971 | Hakim | |
| 3,672,402 A | 6/1972 | Bloemer | |
| 4,112,735 A | 9/1978 | McKnight | |
| 4,138,879 A | 2/1979 | Liebermann | |
| 4,371,786 A | 2/1983 | Kramer | |
| 4,448,538 A | 5/1984 | Mantel | |
| 4,559,454 A | 12/1985 | Kramer | |
| 4,790,653 A | 12/1988 | North, Jr. | |
| 4,818,103 A | 4/1989 | Thomas et al. | |
| 4,844,610 A | 7/1989 | North, Jr. | |
| 5,040,890 A | 8/1991 | North, Jr. | |
| 5,043,706 A | 8/1991 | Oliver | |
| 5,083,862 A | 1/1992 | Rusnak | |
| 5,155,543 A | 10/1992 | Hirako | |
| 5,395,588 A | 3/1995 | North, Jr. et al. | |
| 5,403,552 A | 4/1995 | Pardikes | |

(Continued)

FOREIGN PATENT DOCUMENTS

EP 1521076 4/2005

(Continued)

*Primary Examiner* — Maureen M Wallenhorst
(74) *Attorney, Agent, or Firm* — Jeffrey Schox

(57) ABSTRACT

The fluidic system of the preferred embodiment includes a sheath pump to pump sheath fluid from a sheath container into an interrogation zone, a sheath volume measurement device to measure the fluid in the sheath container, a waste pump to pump the sheath fluid and a sample fluid as waste fluid from the interrogation zone into a waste container, and a waste volume measurement device to measure the fluid in the waste container. The system also includes a controller connected to the sheath pump, the waste pump, and the volume measurement devices. The sheath pump and/or the waste pump draw sample fluid from a sample container into the interrogation zone, which functions to provide a location for the fluidic system and an optical system of the flow cytometer to cooperatively facilitate the analysis of the sample fluid.

22 Claims, 2 Drawing Sheets

U.S. PATENT DOCUMENTS

| | | | |
|---|---|---|---|
| 5,539,386 A | 7/1996 | Elliot | |
| 5,552,885 A | 9/1996 | Steen | |
| 5,797,430 A | 8/1998 | Becke et al. | |
| 6,039,078 A | 3/2000 | Tamari | |
| 6,070,477 A * | 6/2000 | Mark | 73/865.5 |
| 6,110,427 A | 8/2000 | Uffenheimer | |
| 6,156,208 A | 12/2000 | Desjardins et al. | |
| 6,183,697 B1 | 2/2001 | Tanaka et al. | |
| 6,288,783 B1 | 9/2001 | Auad | |
| 6,382,228 B1 | 5/2002 | Cabuz et al. | |
| 6,427,521 B2 | 8/2002 | Jakkula et al. | |
| 6,431,950 B1 * | 8/2002 | Mayes | 451/5 |
| 6,456,769 B1 | 9/2002 | Furusawa et al. | |
| 6,568,271 B2 | 5/2003 | Shah et al. | |
| 6,602,469 B1 | 8/2003 | Maus et al. | |
| 6,694,799 B2 | 2/2004 | Small | |
| 6,718,415 B1 | 8/2004 | Chu | |
| 6,825,926 B2 | 11/2004 | Turner et al. | |
| 6,852,284 B1 | 2/2005 | Holl et al. | |
| 6,872,180 B2 | 3/2005 | Reinhardt et al. | |
| 6,901,964 B2 | 6/2005 | Kippe et al. | |
| 6,908,226 B2 | 6/2005 | Siddiqui et al. | |
| 6,912,904 B2 | 7/2005 | Storm, Jr. et al. | |
| 6,941,005 B2 | 9/2005 | Lary et al. | |
| 7,019,834 B2 | 3/2006 | Sebok et al. | |
| 7,061,595 B2 | 6/2006 | Cabuz et al. | |
| 7,105,355 B2 | 9/2006 | Kurabayashi et al. | |
| 7,328,722 B2 | 2/2008 | Rich | |
| 7,403,125 B2 * | 7/2008 | Rich | 340/603 |
| 7,520,300 B2 | 4/2009 | Rich | |
| 7,628,956 B2 * | 12/2009 | Jindo | 422/81 |
| 2002/0028434 A1 | 3/2002 | Goix et al. | |
| 2002/0059959 A1 | 5/2002 | Qatu et al. | |
| 2002/0123154 A1 | 9/2002 | Burshteyn | |
| 2003/0054558 A1 | 3/2003 | Kurabayashi | |
| 2003/0062314 A1 | 4/2003 | Davidson et al. | |
| 2003/0072549 A1 | 4/2003 | Facer et al. | |
| 2003/0129090 A1 | 7/2003 | Farrell | |
| 2003/0175157 A1 * | 9/2003 | Micklash et al. | 422/70 |
| 2003/0202175 A1 | 10/2003 | Van den Engh et al. | |
| 2003/0211009 A1 | 11/2003 | Buchanan | |
| 2003/0223061 A1 | 12/2003 | Sebok | |
| 2004/0031521 A1 | 2/2004 | Vrane et al. | |
| 2004/0112808 A1 | 6/2004 | Takagi et al. | |
| 2004/0123645 A1 | 7/2004 | Storm, Jr. et al. | |
| 2005/0069454 A1 | 3/2005 | Bell | |
| 2005/0195684 A1 | 9/2005 | Mayer | |
| 2005/0252574 A1 | 11/2005 | Khan et al. | |
| 2006/0177937 A1 | 8/2006 | Kurabayashi et al. | |
| 2006/0286549 A1 | 12/2006 | Sohn et al. | |
| 2007/0003434 A1 | 1/2007 | Padmanabhan et al. | |
| 2007/0212262 A1 * | 9/2007 | Rich | 422/73 |
| 2007/0224684 A1 * | 9/2007 | Olson et al. | 436/63 |
| 2009/0104075 A1 * | 4/2009 | Rich | 422/63 |

FOREIGN PATENT DOCUMENTS

WO 2005017499 8/2005

* cited by examiner

FLOW CYTOMETER SYSTEM WITH SHEATH AND WASTE FLUID MEASUREMENT

CROSS-REFERENCE TO RELATED APPLICATIONS

This application claims the benefit of U.S. Provisional Application No. 60/792,447, filed 17 Apr. 2006 and entitled "Flow Cytometer System with Sheath and Waste Fluid Measurement", which is incorporated in its entirety by this reference.

TECHNICAL FIELD

This invention relates generally to the flow cytometer field, and more specifically to a flow cytometer system with sheath and waste fluid measurement.

BACKGROUND

As flow cytometer systems become smaller and more portable, the sheath fluid containers and the waste fluid containers are becoming correspondingly smaller and more portable. As a result, portable flow cytometer systems may exhaust the supply of sheath fluid or overfill the waste container during the course of an experiment. While refilling or replacing the sheath fluid container and emptying the waste container takes a nominal amount of time and effort, the user must continuously suspend the experiment to ensure that the sheath fluid is not entirely depleted and that the waste container is not overfilled. Should the sheath container become empty, data sampled from or around the time when the sheath fluid ran out may be compromised. Accordingly, a user will typically have to provide a new sample material and run new experiments to ensure the accuracy of the data. Similarly, should the waste container overflow, the user will undoubtedly have to suspend the experiment in order to clean and sterilize the area. As the samples analyzed by flow cytometers vary from relatively benign to much less so, the overflow of the waste container can cause serious delays and perhaps hazardous conditions.

Thus, there is a need for improved flow cytometer flow system that is adapted to determine a volume of the sheath fluid and the waste fluid during operation. This invention provides such an improved and useful flow cytometer system.

DESCRIPTION OF THE PREFERRED EMBODIMENT

The following description of the preferred embodiments of the invention is not intended to limit the invention to these preferred embodiments, but rather to enable any person skilled in the art of flow cytometry to make and use this invention.

Figure 1:
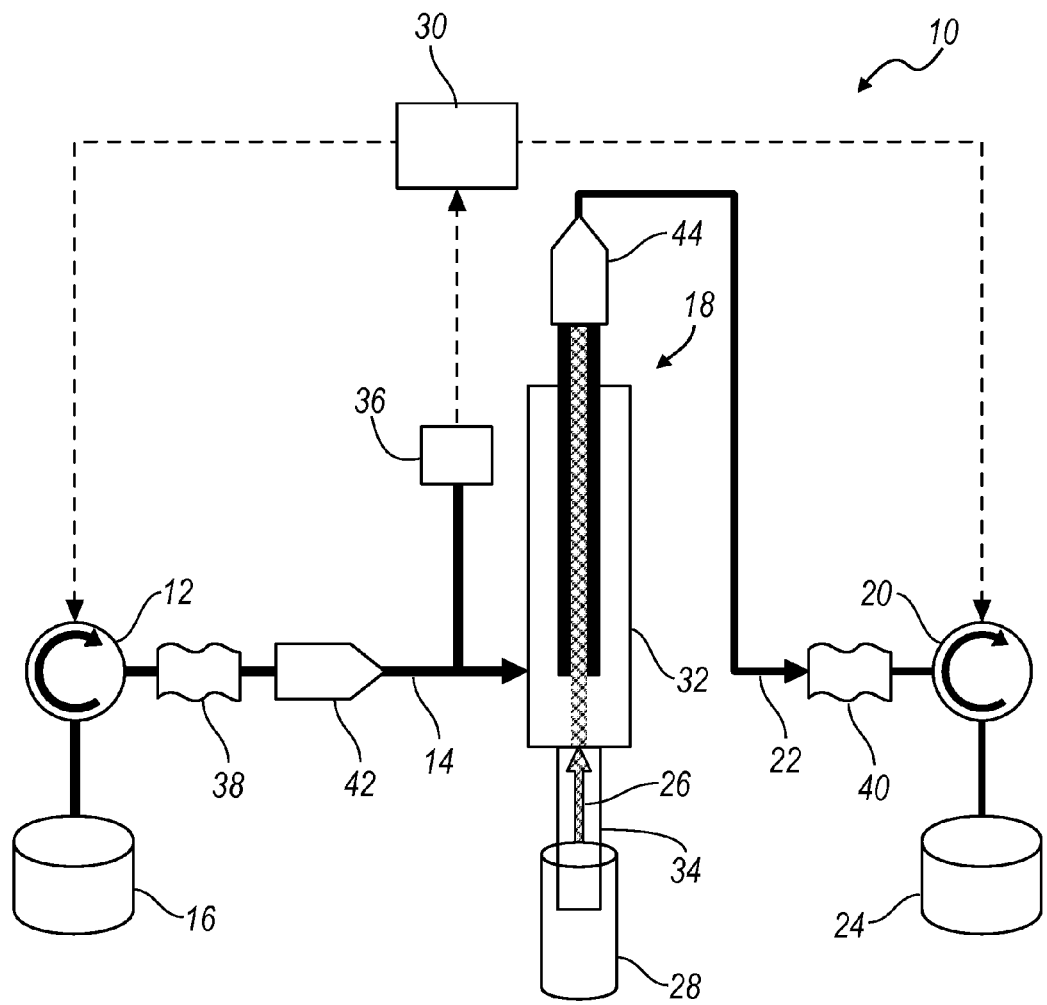
FIG. 1 is a schematic representation of the flow cytometer system with sheath and waste fluid measurement of the preferred embodiment of the invention.

As shown in FIG. 1, the fluidic system 10 of the preferred embodiment includes a sheath pump 12 to pump sheath fluid 14 from a sheath container 16 into an interrogation zone 18, a sheath volume measurement device 38 to measure the fluid in the sheath container 16, a waste pump 20 to pump the sheath fluid 14 and a sample fluid 26 as waste fluid 22 from the interrogation zone 18 into a waste container 24, and a waste volume measurement device 40 to measure the fluid in the waste container 24. The fluidic system 10 also includes a controller 30 connected to the sheath pump 12, the waste pump 20, and the volume measurement devices. The sheath pump 12 and/or the waste pump 20 draw sample fluid 26 from a sample container 28 into the interrogation zone 18. The interrogation zone 18 functions to provide a location for the fluidic system 10 and an optical system of the flow cytometer to cooperatively facilitate the analysis of the sample fluid 26. The fluidic system 10 is preferably incorporated into a flow cytometer, but may be alternatively incorporated into any suitable system.

The sheath pump 12 of the preferred embodiment functions to pump sheath fluid 14 from a sheath container 16 into an interrogation zone 18. The sheath fluid 14 functions to hydrodynamically focus the sample fluid 26. The process of hydrodynamic focusing results in laminar flow of the sample fluid 26 within the flow cell 32 and enables the optical system to illuminate, and thus analyze, the particles within the sample fluid 26 with uniformity and repeatability. Preferably, the sheath fluid 14 is buffered saline or de-ionized water, but the sheath fluid 14 may alternatively be any suitable fluid to hydrodynamically focus the sample fluid 26. The sheath container 16 functions to contain the sheath fluid 14. The sheath container 16 is preferably a vented tank with a volume of approximately 1 L, but the sheath tank may alternatively be any suitable container to contain the sheath fluid 14. The sheath pump 12 may additionally function to pump other fluids into the interrogation zone 18. For example, after the use of the flow cytometer, the sheath pump 12 may pump a bleaching agent from a bleach container into the interrogation zone 18, then pump the sheath fluid 14 from the sheath container 16 into the interrogation zone 18, and finally pump a cleaning agent (such as a detergent or an antimicrobial) from a cleaning container into the interrogation zone 18. Preferably, the sheath pump 12 is a positive displacement pump. More preferably, the sheath pump 12 is a peristaltic pump with a flexible tube and one or more cams that pump the sheath fluid 14 through the flexible tube. The sheath pump 12 preferably has a known flow rate to pump speed ratio, such that control of the speed of the sheath pump 12 corresponds to a control of the flow rate of the sheath fluid 14. With this pump type, the fluidic system 10 is relatively easy to assemble, light to haul, quick to control, and easy to clean. Alternatively, the sheath pump 12 may be any suitable pump that pumps sheath fluid 14 from a sheath container 16 into an interrogation zone 18.

Figure 2:
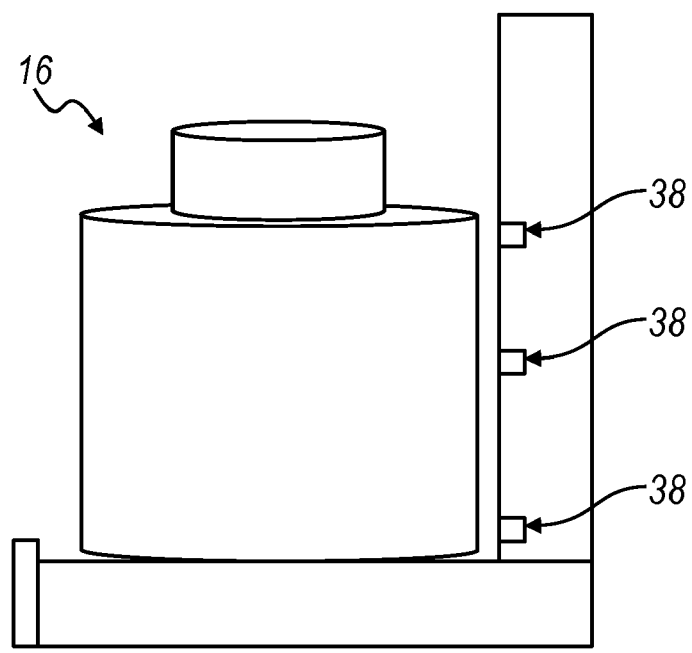
FIGS. 2 and 3 are schematic drawings of the first and second variations respectively, of the volume measurement device of the system.
Figure 3:
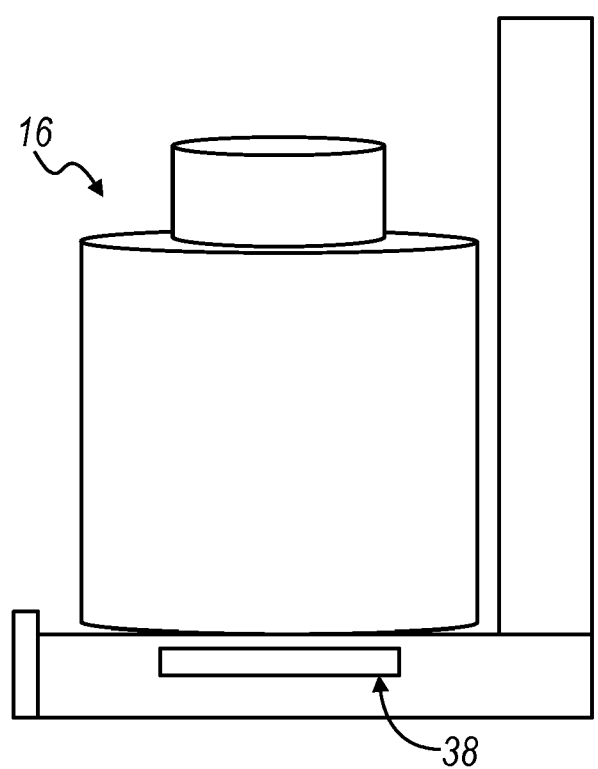

The sheath volume measurement device 38 functions to measure the fluid in the sheath container 16. As shown in FIGS. 2 and 3, the sheath volume measurement device 38 is preferably arranged such that is does not directly contact the sheath fluid 14 in the sheath container 16. Preferably, the sheath volume measurement device 38 is independent from the sheath container 16, such that any size, shape, or material may be used for the sheath container 16 without affecting the accuracy of the volume measurement device. Alternatively, the sheath volume measurement device 38 is dependent on the use of specific containers, as predetermined by the manufacturer or seller of the flow cytometer system.

In a first variation, as shown in FIG. 2, the sheath volume measurement device 38 includes one or more capacitive sensors disposable on or near the sheath container 16. The capacitive sensors preferably sense (1) the discrete presence or absence of a container, and (2) the discrete presence or absence of a fluid at that position. The capacitive sensors may also map a continuous capacitance against a lookup table to estimate the volume of the fluid in the container. Preferably, the capacitive sensors are placed near the top of the container (to indicate that the container is full) and near the bottom of the container (to sense that the container is almost empty). Alternatively, the capacitive sensors may be oriented on or near the container at various elevations to determine the volume of the fluid at multiple points.

In a second variation, as shown in FIG. 3, the sheath volume measurement device 38 includes a scale or other suitable means for measuring the weight of the container and any fluid therein. The weight measured by the sheath volume measurement device 38 is indicative of the volume of fluid within the container, thus any measured weight below a predetermined value (including the tare weight of the container itself) is indicative of the fluid being less than a predetermined volume. Alternatively, the scale may be adapted to provide a consistent signal indicative of the volume of the fluid within the container throughout the use of the system in order to keep a user apprised of the volume of fluid.

In a third variation, the sheath volume measurement device 38 includes any device that is adapted to distinguish between a fluidic volume and an empty air volume, including for example, optical detectors, acoustic detectors, electrical impedance detectors, magnetic inductance detectors, and other suitable devices.

The waste pump 20 of the preferred embodiment functions to pump the waste fluid 22 from the interrogation zone 18 into a waste container 24. Preferably, the waste fluid 22 includes the sheath fluid 14 and the sample fluid 26. Alternatively, the waste fluid 22 may include any fluid that exits the interrogation zone 18. The waste container 24 is preferably a vented tank with a volume of approximately 1 L, but the waste tank may alternatively be any suitable container to contain the waste fluid 22. Like the sheath pump 12, the waste pump 20 is preferably a positive displacement pump and more preferably a peristaltic pump with a flexible tube and one or more cams that pump the waste fluid 22 through the flexible tube. The waste pump 20 preferably has a known flow rate to pump speed ratio, such that control of the speed of the waste pump 20 corresponds to a control of the flow rate of the waste fluid 22. With this pump type, the fluidic system 10 is relatively easy to assemble, light to haul, quick to control, and easy to clean. Alternatively, the waste pump 20 may be any suitable pump that pumps waste fluid 22 from a waste container 24 into an interrogation zone 18.

The waste volume measurement device 40 is preferably identical to the sheath volume measurement device 38, except that it functions to measure the fluid in the waste container 24. The waste volume measurement device 40 is preferably arranged such that is does not directly contact the waste fluid 22 in the waste container 24. Preferably, the waste volume measurement device 40 is independent from the waste container 24, such that any size, shape, or material may be used for the waste container 24 without affecting the accuracy of the volume measurement device. Alternatively, the waste volume measurement device 40 is dependent on the use of specific containers, as predetermined by the manufacturer or seller of the flow cytometer system. The waste volume measurement device 40 may, however, be different than the sheath volume measurement device 38. For example, the sheath volume measurement device 38 may measure the volume of the sheath fluid 14 based on its capacitive or optical properties, while the waste volume measurement device 40 may measure the volume of the waste fluid 22 based on its weight or acoustic properties.

The fluidic system 10 of the preferred embodiment also includes a controller 30 connected to the sheath pump 12, the waste pump 20, and the volume measurement devices. The controller 30 also functions to adjust the flow rate of the sample fluid 26 from the sample container 28 into the interrogation zone 18. The controller 30 functions to receive information regarding the volume of the fluids in the sheath container 16 and the waste container 24. The controller 30 preferably provides an indication to an operator of a low volume of sheath fluid 14 or a high volume of waste fluid 22, as appropriate, to a user of the system. The indication provided by the preferred controller 30 can include visual and aural signals, as well as any other suitable means or methods for automatically communicating the volume measurements to the user. The controller 30 is preferably a proportional-integral-derivative (PID) controller, but may alternatively be a proportional-integral (PI) controller, a proportional-derivative (PD) controller, a proportional (P) controller, or any other suitable controller.

In one variation, the controller 30 may operate the sheath pump 12 and the waste pump 20 in response to the volume of fluid detected by the volume measurement device. For example, in response to a signal indicating a low volume of sheath fluid 14, the controller 30 may suspend operation of the sheath pump 12 in order to prevent further depletion of the sheath fluid 14 while flushing the remaining fluids into the waste container 24. In response to a signal indicating a high volume of waste fluid 22, the controller 30 may suspend operation of the sheath pump 12 to prevent the further introduction of fluids into the system. Moreover, the controller 30 may suspend operation of the waste pump 20 to keep the waste container 24 from overflowing. Alternatively, the controller 30 may temporarily continue operation of the waste pump 20 in order to flush the system of any fluids and prevent any backflow or stagnation that may contaminate the sample fluid 26. Alternatively, the controller 30 may suspend operation of one or more of the pumps in response to an anticipated high or low volume event. For example, the controller 30 may suspend operation of the sheath pump 12 in response to a predetermined volume measurement from the waste container 24 volume measurement device, wherein the predetermined volume measurement corresponds to a threshold volume that provides for all of the fluids downstream of the sheath pump 12 to be safely deposited into the waste container 24.

The controller 30 may operate the sheath pump 12 and the waste pump 20 in response to the volume of fluid detected by the volume measurement device in several variations. In a first variation, the sheath pump 12 and the waste pump 20 are driven by a single motor, but with a variable drive ratio device (e.g., transmission), such that the sheath pump 12 and the waste pump 20 may be operated at different pump speeds and, therefore, allow for a variable flow rate of the sheath fluid 14 and/or the waste fluid 22. The preferred controller 30 is preferably coupled to the variable drive ratio device such that the controller 30 can vary the relative flow rates of the sheath pump 12 and the waste pump 20.

In a second and third variation, the fluidic system 10 of the preferred embodiment may also include a valve 42 located before the interrogation zone 18 and a valve 44 located after the interrogation zone 18. The valves 42 and 44 function to facilitate the control of the sheath fluid 14 and the waste fluid 22. The valves 42 and 44 are preferably check-valves, but may alternatively be any suitable valve to facilitate the control of the sheath fluid 14 and the waste fluid 22 such as by-pass valves, restrictive valves, and/or shutoff valves.

In a second variation, the sheath pump 12 and the waste pump 20 are driven by a single motor, but the fluidic system 10 includes at least one by-pass valve located near the sheath pump 12 and/or the waste pump 20. The by-pass valve diverts a variable amount of the fluid flow and, therefore, allows for a variable flow rate of the sheath fluid 14 and/or waste fluid 22. The preferred controller 30 is coupled to the by-pass valve and adapted to divert a variable amount of fluid through the by-pass valve.

In a third variation, the sheath pump 12 and the waste pump 20 are driven by a single motor, but the fluidic system 10 includes at least one restrictive valve located near the sheath pump 12 and/or the waste pump 20. The restrictive valve alters the fluid flow and, therefore, allows for a variable flow rate of the sheath fluid 14 and/or waste fluid 22. The restrictive valve maybe a shutoff valve that alters the fluid flow and, therefore, allows for a variable flow rate of the sheath fluid and/or waste fluid. The preferred controller 30 is coupled to the restrictive valve and adapted to open/close the shutoff valve.

In a fourth variation, the sheath pump 12 and the waste pump 20 are driven by separate motors with separate controls and, therefore, allow for a variable flow rate of the sheath fluid 14 and/or waste fluid 22. The preferred controller 30 is preferably coupled to one or both of the separate controls of the respective pumps. The fluidic system 10 may, however, include other suitable variations that draw the sample fluid 26 from the sample container 28 into the interrogation zone 18 through the use of a pressure differential.

As a person skilled in the art of flow cytometry will recognize from the previous detailed description and from the figures and claims, modifications and changes can be made to the preferred embodiments of the invention without departing from the scope of this invention defined in the following claims.

I claim:

1. A fluidic system for a flow cytometer with an interrogation zone, the fluidic system comprising:
    a pump subsystem that pumps sheath fluid from a sheath container into the interrogation zone of the flow cytometer, sample fluid from a sample container into the interrogation zone of the flow cytometer, and waste fluid from the interrogation zone into a waste container;
    a volume measurement device including a capacitive sensor coupled to at least one measured container, the measured container being the sheath container or waste container, wherein the volume measurement device measures the volume of fluid in the measured container and wherein the capacitive sensor operates in the following modes:
        a container sense mode—wherein the capacitive sensor senses the discrete presence or absence of the at least one measured container, and
        a fluid sense mode—wherein the capacitive sensor senses the discrete presence or absence of a fluid inside the at least one measured container; and
    a controller coupled to the pump subsystem that adjusts the flow rate of one or more of the sheath fluid, the sample fluid, and the waste fluid based on the volume measurement of the fluid in the at least one measured container.

2. The fluidic system of claim 1 wherein the pump subsystem includes a sheath pump that pumps sheath fluid from the sheath container and sample fluid from the sample container into the interrogation zone of the flow cytometer; and wherein the controller is coupled to the sheath pump.

3. The fluidic system of claim 2 wherein the pump subsystem further includes a waste pump that pumps waste fluid from the interrogation zone into the waste container; wherein at least one of the sheath pump and the waste pump draws sample fluid from a sample container into the interrogation zone; and wherein the controller is coupled to the waste pump.

4. The fluidic system of claim 1 wherein the volume measurement device is a sheath volume measurement device that measures the fluid in the sheath container.

5. The fluidic system of claim 4 further including a second volume measurement device wherein the second volume measurement device is a waste volume measurement device that measures the fluid in the waste container.

6. The fluidic system of claim 5 wherein the controller adjusts the flow rate of one or more of the sheath fluid and the sample fluid by operating in the following mode:
    suspend sheath pump mode—wherein the controller suspends operation of a sheath pump in response to information indicating a low sheath fluid volume event corresponding to a threshold fluid volume.

7. The fluidic system of claim 6 wherein the controller adjusts the flow rate of one or more of the sheath fluid and the sample fluid by operating in the additional following mode:
    suspend waste pump mode—wherein the controller suspends operation of a waste pump in response to information indicating a high waste fluid volume event corresponding to a threshold fluid volume.

8. The fluidic system of claim 1 wherein the controller provides an indication of a low sheath fluid volume event or a high waste fluid volume event, each event corresponding to a threshold fluid volume, based on information regarding the volume of the fluids received from the volume measurement device.

9. The fluidic system of claim 8 wherein the indication is a visual signal.

10. The fluidic system of claim 1 wherein the volume measurement device is independent from the at least one measured container and does not contact fluid in the at least one measured container.

11. The fluidic system of claim 1 wherein the capacitive sensor further includes a look-up table and the capacitive sensor senses a continuous capacitance and maps the capacitance against the lookup table to determine the volume of the fluid in the measured container.

12. The fluidic system of claim 1 wherein the capacitive sensor is placed at the top portion of the measured container such that it senses when the measured container is substantially full.

13. The fluidic system of claim 1 wherein the capacitive sensor is placed at the bottom portion of the measured container such that it senses when the measured container is substantially empty.

14. The fluidic system of claim 1 wherein the capacitive sensor is placed at a first elevation relative to the at least one measured container to determine the presence of the fluid at a first point.

15. The fluidic system of claim 14 further including a second capacitive sensor wherein the second capacitive sensor is placed at a second elevation relative to the at least one measured container to determine the presence of the fluid at a second point.

16. The fluidic system of claim 1 wherein the volume measurement device further includes a detector selected from the group consisting of optical detectors, acoustic detectors, electrical impedance detectors, magnetic inductance detectors, and combinations thereof such that the detector distinguishes between a fluidic volume and an empty air volume.

17. The fluidic system of claim 1 wherein the controller adjusts the relative flow rates of at least a sheath pump and a waste pump based on the measurement of the fluid in the measured container.

18. The fluidic system of claim 17, further comprising a motor and a variable drive ratio device coupled to the motor that drives the sheath pump and the waste pump, wherein the controller is coupled to the variable drive ratio device.

19. The fluidic system of claim 17, further comprising a first motor and a second motor that drive the sheath pump and the waste pump, respectively, wherein the controller is coupled to at least one of the first and second motors.

20. The fluidic system of claim 1, further comprising a first valve located before the interrogation zone and a second valve located after the interrogation zone, wherein the controller is coupled to at least one of the first and second valves.

21. A fluidic system for a flow cytometer with an interrogation zone, the fluidic system comprising:
a pump subsystem including a sheath pump that pumps sheath fluid from a sheath container into the interrogation zone of the flow cytometer and a waste pump that pumps waste fluid from the interrogation zone into a waste container, wherein at least one of the sheath pump and the waste pump draws sample fluid from a sample container into the interrogation zone of the flow cytometer;
a volume measurement device coupled to at least one measured container, the measured container being the sheath container or waste container and wherein the volume measurement device measures the volume of fluid in the measured container; and wherein the volume measurement device includes at least one capacitive sensor adjacent to the measured container, wherein the at least one capacitive sensor operates in the following modes:
container sense mode—wherein the at least one capacitive sensor senses the discrete presence or absence of the at least one measured container, and
fluid sense mode—wherein the at least one capacitive sensor senses the discrete presence or absence of a fluid inside the at least one measured container, and
a controller, coupled to the sheath pump, the waste pump, and the volume measurement device, that adjusts the relative flow rates of the sheath pump and the waste pump based on the volume measurement of the fluid in the at least one measured container.

22. The fluidic system of claim 21 wherein the volume measurement device includes a scale adjacent to the at least one measured container such that the scale measures the weight of the measured container and the weight of any fluid therein.

* * * * *